United States Patent [19]

Montzka et al.

[11] 4,246,413
[45] Jan. 20, 1981

[54] 6-OXAMORPHINANS

[75] Inventors: Thomas A. Montzka, Manlius; John D. Matiskella; Richard A. Partyka, both of Liverpool, all of N.Y.

[73] Assignee: Bristol-Myers Company, New York, N.Y.

[21] Appl. No.: 38,995

[22] Filed: May 14, 1979

[51] Int. Cl.$^3$ ............... C07D 491/08; C07D 491/107; A61K 31/445
[52] U.S. Cl. ...................................... 546/63; 546/15; 546/97; 424/256
[58] Field of Search ................... 424/256; 546/63, 15

[56] References Cited

U.S. PATENT DOCUMENTS

| | | | |
|---|---|---|---|
| 3,853,889 | 12/1974 | Monkovic et al. | 546/63 |
| 3,959,290 | 5/1976 | Monkovic et al. | 546/63 |
| 4,016,167 | 4/1977 | Montzka et al. | 546/63 |
| 4,154,932 | 5/1979 | Montzka et al. | 546/63 |

Primary Examiner—Donald G. Daus
Assistant Examiner—Diana G. Rivers
Attorney, Agent, or Firm—Richard R. Lloyd

[57] ABSTRACT

Substituted 6-oxamorphinans and 6-oxaisomorphinans have been found to possess potent analgetic, narcotic antagonist, antitussive and/or ADH inhibitory activity. The compounds are prepared by total synthesis and are not derived from opium alkaloids.

13 Claims, No Drawings

6-OXAMORPHINANS

SUMMARY OF THE INVENTION

6-Oxamorphinans and 6-Oxaisomorphinans of the formula

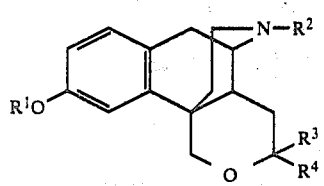

wherein $R^1$ is hydrogen, (lower)alkyl, (lower)alkanoyl or nicotinoyl; $R^2$ is hydrogen, (lower)alkyl, propargyl, allyl, 3,3-dimethylallyl, cyclopropylmethyl, cyclobutylmethyl,

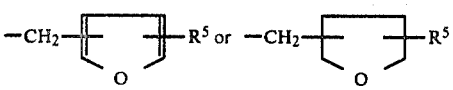

in which $R^5$ is hydrogen or (lower)alkyl, and $R^3$ and $R^4$ are the same or different and are (lower)alkyl, or $R^3$ and $R^4$, when taken together with the carbon atom to which they are attached, represent a spiroalkyl group of from 4 to 6 carbon atoms or a spiro moiety of the formula

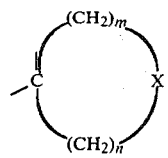

in which X is oxygen or sulfur, m is 2 or 3 and n is 1 or 2; and pharmaceutically acceptable salts thereof, possess analgetic, narcotic antagonist, antitussive and/or ADH inhibitory activity, or are useful intermediates in the preparation of such compounds.

DESCRIPTION OF THE PRIOR ART

U.S. Pat. No. 3,853,889 discloses substituted 8-oxamorphinans and 8-oxaisomorphinans having the formula

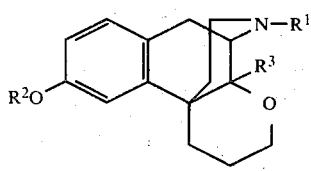

wherein $R^1$ is H, (lower)alkyl, (lower)alkenyl,

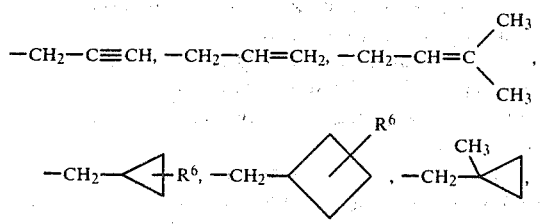

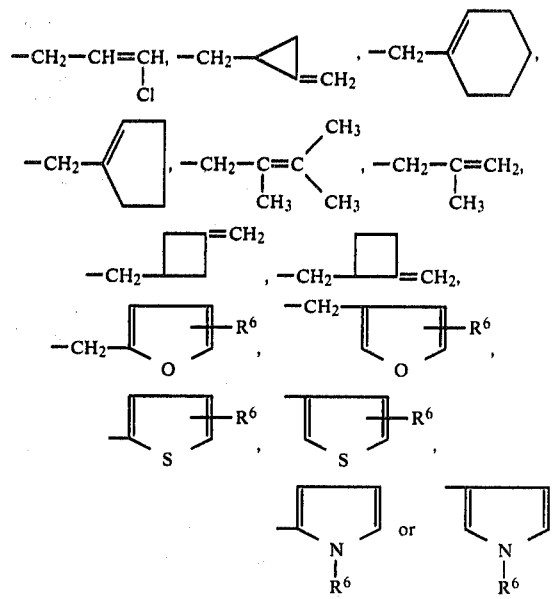

in which $R^6$ is H or $CH_3$; $R^2$ is H, (lower)alkyl, (lower)-alkanoyl, cinnamoyl,

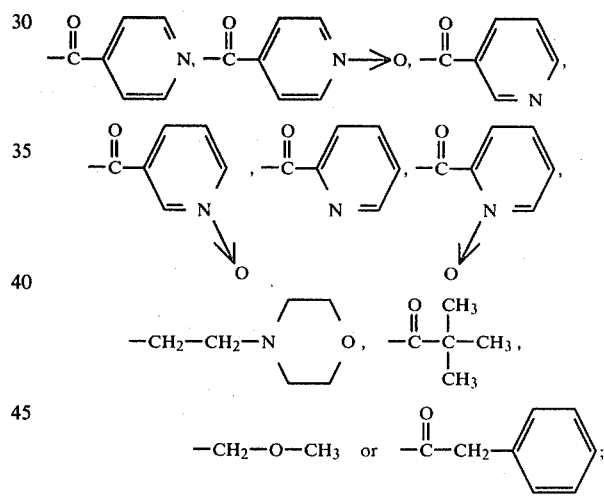

and $R^3$ is H or (lower)alkyl; and pharmaceutically acceptable acid addition salts thereof. The compounds are stated to be analgetic agents, narcotic antagonists or intermediates in the preparation of such agents. U.S. Pat. No. 3,959,290, a continuation-in-part of the above-identified patent, has a substantially identical disclosure.

U.S. Pat. No. 4,016,167 discloses substituted 6,8-dioxamorphinans and 6,8-dioxaisomorphinans having the formula

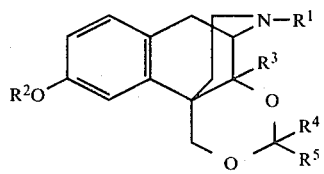

wherein $R^1$ is H, (lower)alkyl, (lower)alkenyl,

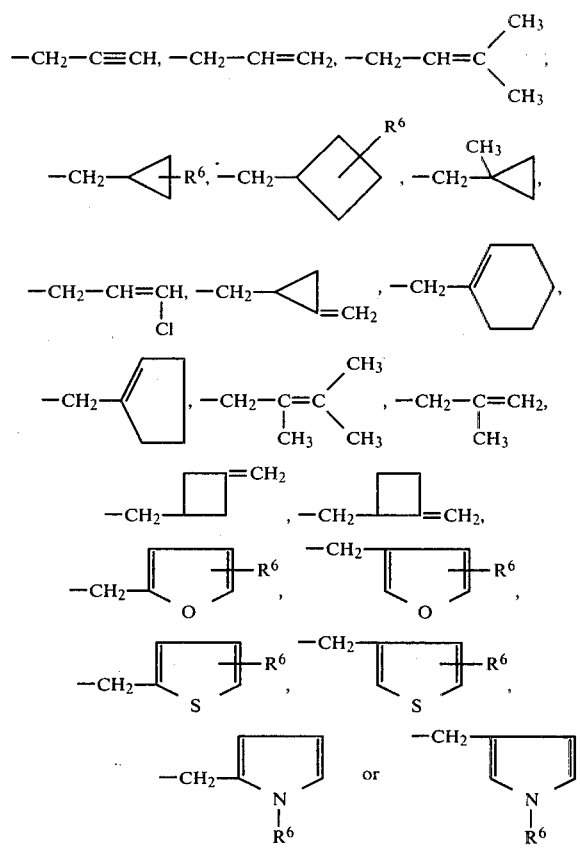

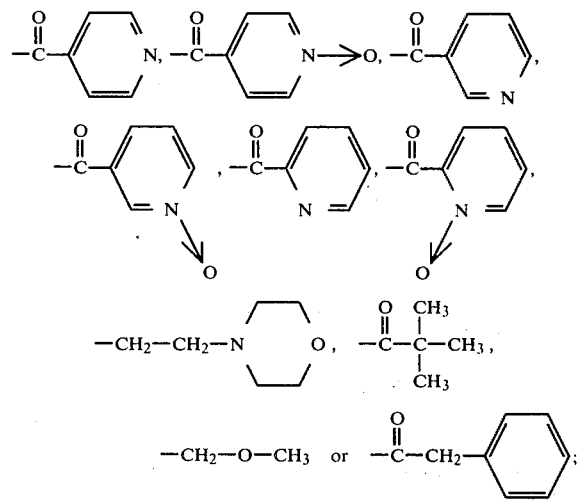

in which $R^6$ is H or $CH_3$; $R^2$ is H, (lower)alkyl, (lower)-alkanoyl, cinnamoyl, $R^3$ is H or (lower)alkyl; and $R^4$ and $R^5$ are alike or different and each is H, (lower)alkyl or trifluoromethyl, or when taken together $R^4$ and $R^5$ are a carbonyl function or a spiroalkyl group of 3 to 7 carbon atoms; and pharmaceutically acceptable acid addition salts thereof. The compounds are stated to possess analgetic agonist-/antagonist activity or to be useful intermediates. Other prior art is cited in columns 1–4 of this patent.

COMPLETE DISCLOSURE

This invention relates to substituted 6-oxamorphinans and 6-oxaisomorphinans of the formula

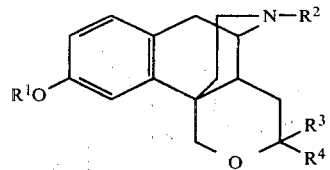

wherein $R^1$ is hydrogen, (lower)alkyl, (lower)alkanoyl or nicotinoyl; $R^2$ is hydrogen, (lower)alkyl, propargyl, allyl, 3,3-dimethylallyl, cyclopropylmethyl, cyclobutylmethyl,

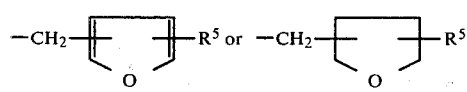

in which $R^5$ is hydrogen or (lower)alkyl, and $R^3$ and $R^4$ are the same or different and are (lower)alkyl, or $R^3$ and $R^4$, when taken together with the carbon atom to which they are attached, represent a spiroalkyl group of from 4 to 6 carbon atoms or a spiro moiety of the formula

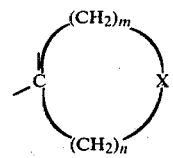

in which X is oxygen or sulfur, m is 2 or 3 and n is 1 or 2; and pharmaceutically acceptable salts thereof, and to their total synthesis from the known compound, 6-carbo-methoxy-8-methoxy-3-methyl-11-oxo-1,2,3,4,5,6-hexahydro-2,6-methano-3-benzazocine [5-carbomethoxy-2′-methoxy-2-methyl-9-oxo-6,7-benzomorphan].

Drug abuse by thrill-seeking youth or by people looking for an escape from the realities of everyday life has become more and more commonplace in our present society. One class of widely abused drugs are the narcotic analgetics such as codeine, morphine, meperidine, etc.. It is because of the high addictive potential of these agents that much time and money are being expended by the pharmaceutical industry and by governments to try and discover and develop new nonaddicting analgetics and/or narcotic antagonists.

It was therefore an object of the present invention to find novel low abuse analgetics and/or narcotic antagonists. It was a further object of the present invention to develop a method of synthesis that would not be dependent upon opium alkaloids as starting materials.

The objects of the present invention have been met by the provision of the compounds of Formula I and by their total synthesis from 6-carbomethoxy-8-methoxy-3-methyl-11-oxo-1,2,3,4,5,6-hexahydro-2,6-methano-3-benzazocine.

The compounds of Formula I have the basic 6-oxamorphinan nucleus which is numbered and represented by the following plane formula:

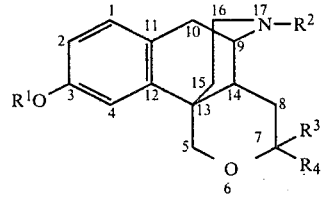

When $R^3$ and $R^4$ are alike, there are three asymmetric carbon atoms in the morphinan molecule (carbons 9, 13 and 14), which result in two diastereoisomeric racemates (four optical isomers) because the iminoethano system attached to carbons 9 and 13 is geometrically constrained to a cis-1,3-diaxial fusion. However, when $R^3$ and $R^4$ are not alike, then carbon 7 also becomes asymmetric. This results in four diastereoisomeric racemates or a total of eight optical isomers.

The present invention includes both the 6-oxamorphinans and the 6-oxaisomorphinans, either as their diastereoisomeric and/or d,l (racemic) mixtures or as their resolved optical isomers. The d- and l-isomers may be separated and isolated by fractional crystallization of the diastereoisomeric salts formed by the reaction of the racemic mixture with, for instance, d- or l-tartaric acid or D-(+)-α-bromocamphorsulfonic acid. Alternatively, one may obtain the desired d- or l- form of a compound of Formula I by utilizing the pure d- or l- form of the starting 6-carbomethoxy-8-methoxy-3-methyl-11-oxo-1,2,3,4,5,6-hexahydro-2,6-methano-3-benzazocine. The 6-oxamorphinans are the preferred series of compounds and the (−)-isomers of the compounds are the preferred isomers.

In a preferred embodiment of this invention the compounds have the structure of Formula I in which $R^1$ is hydrogen or (lower)alkyl, $R^2$ is hydrogen, (lower)alkyl, cyclopropylmethyl or cyclobutylmethyl, and $R^3$ and $R^4$ are the same or different and are each (lower)alkyl.

In a more preferred embodiment of this invention the compounds have the structure of Formula I in which $R^1$ is hydrogen or methyl, $R^2$ is hydrogen, methyl, cyclopropylmethyl or cyclobutylmethyl, and $R^3$ and $R^4$ are each methyl.

In a most preferred embodiment of this invention, the compounds have the structure of Formula I in which $R^1$ is hydrogen, $R^3$ and $R^4$ are methyl, and $R^2$ is cyclobutylmethyl (and most preferably the (−)-isomer thereof).

In another most preferred embodiment of this invention, the compounds have the structure of Formula I in which $R^1$ is hydrogen, $R^3$ and $R^4$ are methyl, and $R^2$ is cyclopropylmethyl (and most preferably the (−)-isomer thereof).

In another most preferred embodiment of this invention, the compounds have the structure of Formula I in which $R^1$, $R^3$ and $R^4$ are methyl, and $R^2$ is cyclobutylmethyl (and most preferably the (−)-isomer thereof).

In another most preferred embodiment of this invention, the compounds have the structure of Formula I in which $R^1$, $R^3$ and $R^4$ are methyl, and $R^2$ is cyclopropylmethyl (and most preferably the (−)-isomer thereof).

In still another most preferred embodiment of this invention, the compounds have the structure of Formula I in which $R^1$, $R^3$ and $R^4$ are methyl, and $R^2$ is hydrogen (and most preferably the (−)-isomer thereof).

The compounds of this invention are prepared by a total synthesis comprising multiple steps, as outlined in Chart I for certain of the preferred embodiments of this invention in which $R^3$ and $R^4$ are each methyl.

Chart I

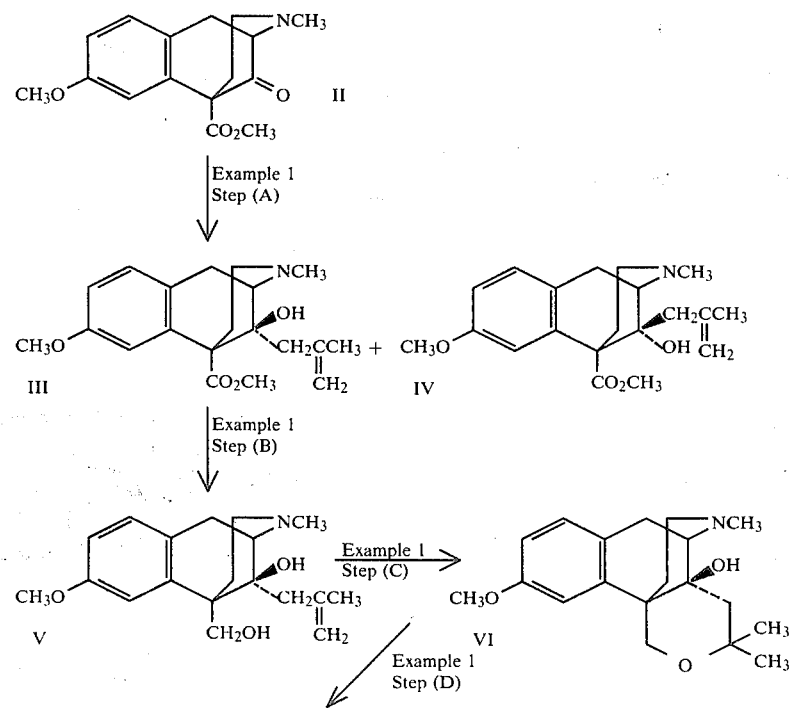

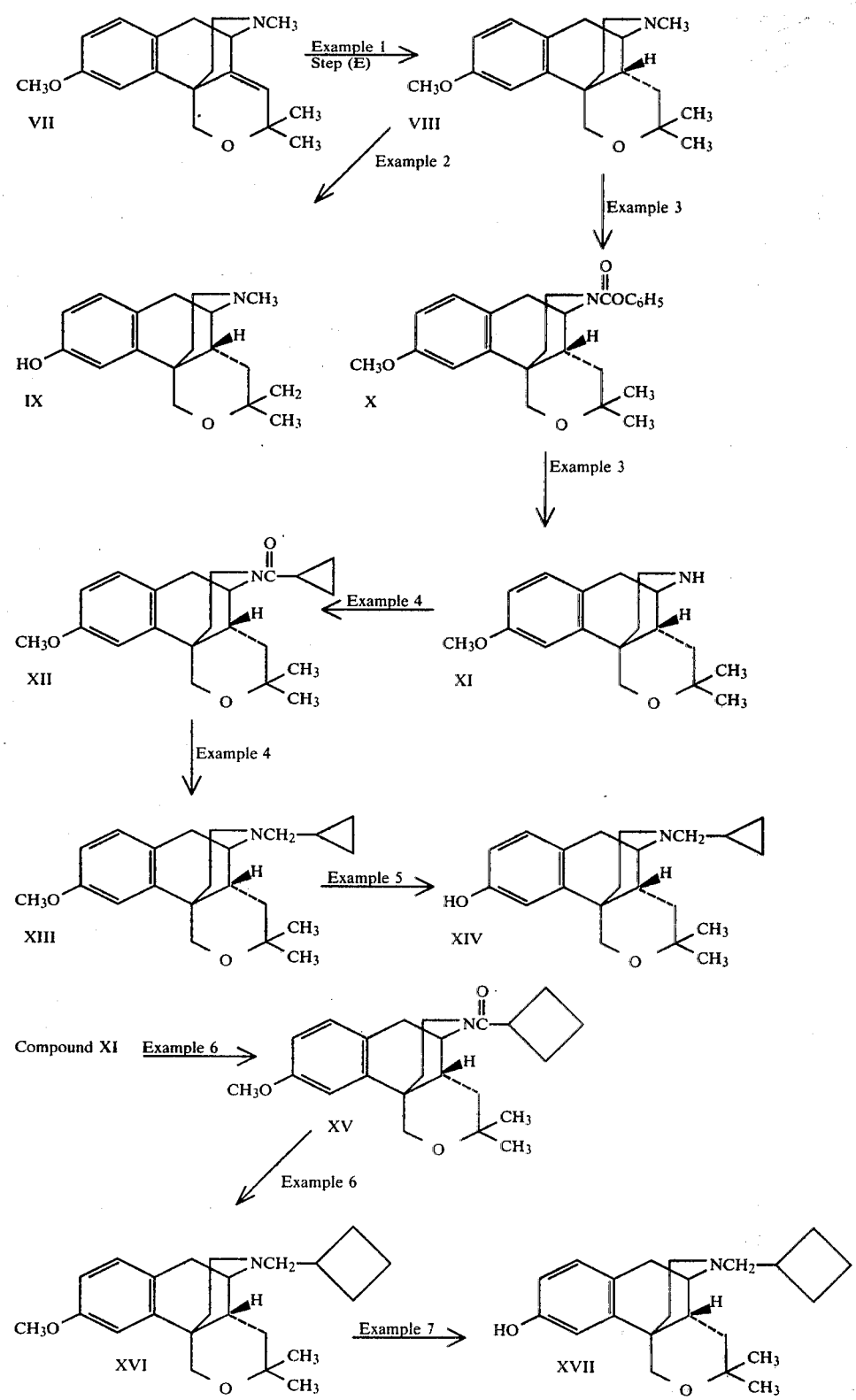
In another aspect, this invention relates to a process for the preparation of substituted 6-oxamorphinans and 6-oxaisomorphinans of the formula

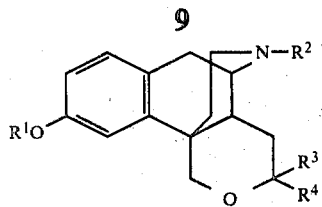

wherein $R^1$ is hydrogen, (lower)alkyl, (lower)alkanoyl or nicotinoyl; $R^2$ is hydrogen, (lower)alkyl, propargyl, allyl, 3,3-dimethylallyl, cyclopropylmethyl, cyclobutylmethyl,

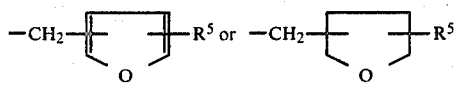

in which $R^5$ is hydrogen or (lower)alkyl, and $R^3$ and $R^4$ are the same or different and are (lower)alkyl, or $R^3$ and $R^4$, when taken together with the carbon atom to which they are attached, represent a spiroalkyl group of from 4 to 6 carbon atoms or a spiro moiety of the formula

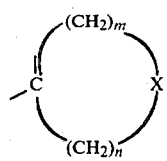

in which X is oxygen or sulfur, m is 2 or 3 and n is 1 or 2; and pharmaceutically acceptable salts thereof, which process comprises the consecutive steps of (A) treating a compound of the formula

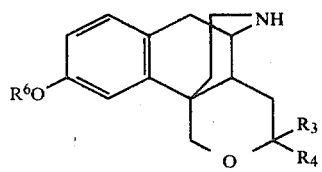

in which $R^3$ and $R^4$ are as defined above, and $R^6$ is (lower)alkyl, with an alkylating or acylating agent of the formula

wherein W is hydrogen, (lower)alkyl, cyclopropyl, cyclobutyl,

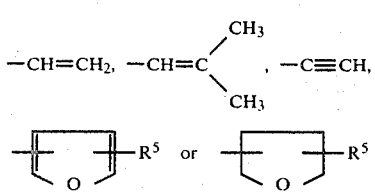

in which $R^5$ is hydrogen or (lower)alkyl; Y is

or —CH$_2$— and X is chloro, bromo or iodo; in an inert organic solvent, in the presence of an appropriate base, to produce a compound having the formula

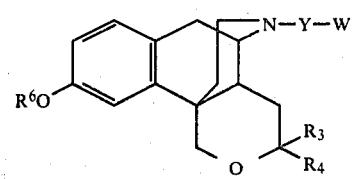

in which $R^3$, $R^4$, $R^6$, Y and W are as defined above, and when Y is a carbonyl moiety (B) treating Compound XIX with a reducing agent selected from lithium aluminum hydride, aluminum hydride, diborane, and sodium bis(2-methoxyethoxy)aluminum hydride, in an inert organic solvent, to produce a compound having the formula

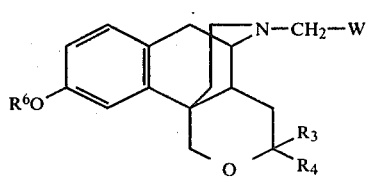

in which $R^3$, $R^4$, $R^6$ and W are as defined above, and when desired (C) cleaving the ether function of Compound XIX or XX with sodium thiomethoxide, sodium thioethoxide, lithium thiomethoxide, lithium thioethoxide, hydrobromic acid, boron tribromide or pyridine hydrochloride, to produce a compound having the formula

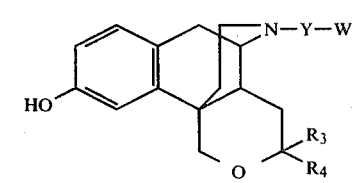

in which $R^3$, $R^4$, Y and W are as defined above, and if desired (D) acylating Compound XXI with an acylating derivative of an acid of the formula

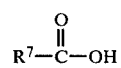

in which $R^7$ is (lower)alkyl or 3-pyridyl, in an inert organic solvent, to produce a compound of the formula

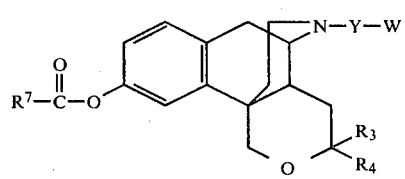

in which $R^3$, $R^4$, $R^7$, Y and W are as defined above.

In starting material XVIII for the above process, $R^6$ is (lower)alkyl. In Chart I, above, the initial starting material (Compound II) contains a methoxy group in the corresponding position and thus produces the compound of Formula XI, which also contains a methoxy group in the corresponding position (i.e. a compound of Formula XVIII in which $R^6$ is methyl), for use as the starting material in the above process. Compounds of Formula XVIII in which $R^6$ is (lower)alkyl other than methyl may be prepared by methods well known to those skilled in the art. For purposes of illustration, the following Chart II shows a procedure utilizing Compound X to prepare a compound of Formula XVIII in which $R^6$ is ethyl. The corresponding propyl, butyl, etc. compounds may be prepared in a similar manner by utilizing the appropriate alkyl halide, e.g. propyl bromide, butyl bromide, etc.

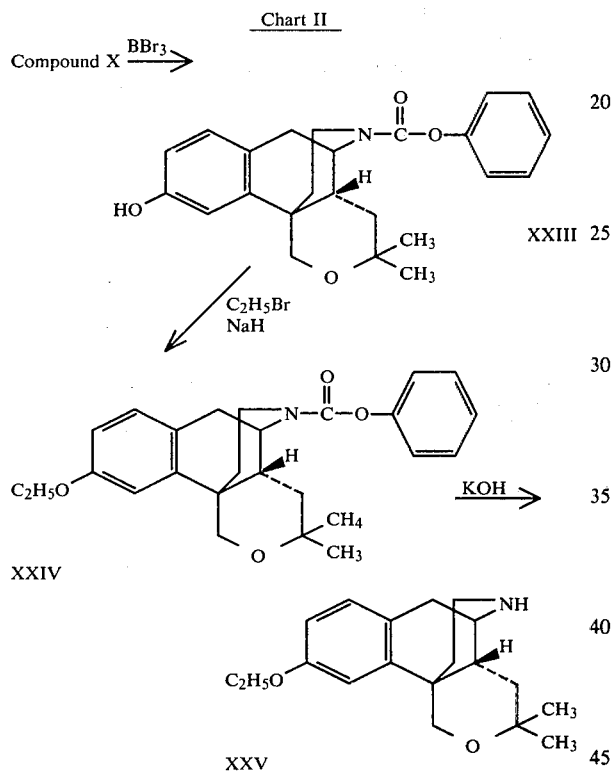

Chart II

For the purpose of this disclosure the term "inert organic solvent" means an organic solvent that does not participate in the reaction to the extent that it emerges unchanged from the reaction. Suitable solvents for process Steps (A) and (D), above, include methylene chloride, chloroform, dichloroethane, tetrachloromethane, benzene, toluene, ether, ethyl acetate, xylene, tetrahydrofuran, dioxane, dimethylacetamide, dimethylformamide, and the like when an acid halide is employed. When an alkylation reaction is being performed, the inert solvent used may also include (lower)alkanols such as methanol, ethanol, n-propanol, isopropanol and the like.

Acceptable inert organic solvents for use in the reduction step (B) in the above process include among others, diethyl ether, dioxane, tetrahydrofuran, benzene, xylene, toluene and the like.

In cleavage step (C), above, suitable solvents will be apparent to those skilled in the art. Thus, when using sodium thiomethoxide, lithium thiomethoxide, sodium thioethoxide or lithium thioethoxide, suitable solvents include dimethylformamide, toluene, xylene, hexamethylphosphoramide and the like. When using boron tribromide, suitable solvents include methylene chloride, ether, chloroform, dichloroethane, carbon tetrachloride and the like. Hydrobromic acid may be utilized, for example in aqueous solution (e.g. 48%) or in acetic acid solution. Pyridine hydrochloride may conveniently be used in excess, where it serves as its own solvent.

The term "appropriate base" includes inorganic bases such as NaOH, KOH, $K_2CO_3$, $Na_2CO_3$, $NaHCO_3$, $KHCO_3$, and the like, and those tertiary amines commonly employed as a proton acceptor in acylation reactions. Such amines are tri(lower)alkylamines, e.g. trimethylamine, triethylamine, and the like, pyridine, dimethylaniline, N-methylpiperidine, and the like.

For the purpose of this disclosure and the appended claims, the term (lower)alkyl is defined as a straight or branched chain alkyl group containing from 1 to 6 carbon atoms, e.g. methyl, propyl, isobutyl, etc.. The term (lower)alkanoyl is defined as a straight or branched chain alkanoyl radical containing from 2 to 6 carbon atoms, e.g. acetyl, propionyl, isobutyryl, etc. The term pharmaceutically acceptable salt is defined as a salt of a compound of this invention with any of the inorganic or organic acids which are commonly used to produce nontoxic salts of medicinal agents containing amine functions. Illustrative examples would be those salts formed by mixing the compounds of Formula I with hydrochloric, sulfuric, nitric, phosphoric, phosphorous, hydrobromic, maleic, malic, ascorbic, citric, tartaric, pamoic, lauric, stearic, palmitic, oleic, myristic, lauryl sulfuric, naphthalenesulfonic, linoleic or linolenic acid, or the like.

Salts of the free bases may be prepared by conventional means, e.g. by addition of the appropriate acid to a solution of the free base in ethanol, 1-propanol, 2-propanol, acetone-methanol, acetone-ethanol, or the like. Salts of the compounds may be converted to the free base by treatment of the salt with dilute $K_2CO_3$ or $Na_2CO_3$ and extraction with $CH_2Cl_2$. The extract is dried with $MgSO_4$, $Na_2SO_4$ or $K_2CO_3$ and then concentrated to give the free base (generally in 100% yield).

All of the compounds of this invention are novel and valuable for their properties as analgetic and/or narcotic antagonist agents, or as intermediates in the preparation of compounds having these biological properties. Some of these compounds also possess potent antitussive or ADH (anti diuretic hormone) inhibitory activity.

It is well known in the narcotic analgesic prior art that it is possible for some compounds to possess both agonist and antagonist properties. An agonist is a compound that imitates a narcotic analgesic and possesses analgetic qualities. An antagonist is a compound that counteracts the analgetic and euphoric properties of a narcotic analgetic. It is possible for a compound to have both properties. A good example of such a compound is cyclazocine.

Table 1 compares the agonist activity of three of the preferred embodiments of this invention with the agonist activity of morphine sulfate, in the standard phenylquinone-induced writhing test [E. A. Siegmund et al., Proc. Soc. Biol. & Med., 95, 729 (1957)]. By the subcutaneous route in mice, BL-6028, BL-6092 and BL-6097 were about 4.9, 6.8 and 3.1 times more potent, respectively, than morphine sulfate. Orally, in mice, BL-6097 was about 8.9 times as potent as morphine sulfate.

Table 1

| Test Compound | Agonist Activity (ED50 in mg/kg) | |
|---|---|---|
| | Mice (SC) | Mice (PO) |
| (±)-VIII (BL-6028) | 0.053 | — |
| (±)-IX (BL-6092) | 0.038 | — |
| (±)-XIV (BL-6097) | 0.083 | 0.35 |
| morphine sulfate | 0.26 | 3.1 |

In the standard oxymorphone-induced Straub tail test for antagonist activity, Compound (±)-XIV (BL-6097) was found to have a subcutaneous $ED_{50}$ of 0.8 mg/kg, or about 1.2 times the antagonist activity of butorphanol.

This invention is illustrated by, but is in no way limited by, the following examples. All temperatures therein are given in °Centigrade.

EXAMPLE 1

3-Methoxy-7,7,17-trimethyl-6-oxamorphinan Hydrochloride (VIII, BL-6028A)

(A)

6-Carbomethoxy-11β-hydroxy-8-methoxy-3-methyl-11α-(2-methylallyl)-1,2,3,4,5,6-hexahydro-2,6-methano-3-benzazocine Hydrochloride (III) And
6-Carbomethoxy-11α-hydroxy-8-methoxy-3-methyl-11β-(2-methylallyl)-1,2,3,4,5,6-hexahydro-2,6-methano-3-benzazocine Hydrogen Oxalate (IV)

An ice-cooled mixture of magnesium chips (30 g) in 50 ml of THF was treated with 5 ml of a solution of 2-methylallyl chloride (10 g; 0.11 mole) in 80 ml of THF. After the reaction started, the remainder of the solution was added over ½ hour period and the mixture was stirred with cooling for 1 hour more. The above Grignard reagent was filtered through glass wool and added to a solution of Compound II [prepared as described in U.S. Pat. No. 4,016,167] (17.4 g; 0.06 mole) in 120 ml of THF maintained at $-45°$ C. (dry ice-$CH_3CN$ bath) over 15 minutes. After 1 hour at $-45°$ C. the reaction was treated with 250 ml of 10% $NH_4Cl$ solution. The layers were separated and the aqueous layer extracted further with ether. Drying and concentration of the organic extracts gave an oil (21.5 g) containing ~55% of Compound III. This material was taken up in 200 ml 1-propanol and treated with 7 g fumaric acid. The crystals (12.2 g) were collected and recrystallized from 1-propanol to give material of sufficient purity (>93%) for use in Step B. A small sample was converted to a hydrochloride salt and crystallized from 2-propanol-acetone for analysis, purity by GLC analysis >97%, mp 196°–200°.

Anal. calcd for $C_{20}H_{27}NO_4.HCl$: C, 62.90; H, 7.39; N, 3.67.

Found: C, 62.68; H, 7.26; N, 3.65.

The mother liquors from the above experiment were concentrated, treated with dilute $K_2CO_3$ and extracted with $CH_2Cl_2$ to give an oil containing Compounds III and IV, and an unknown product. Chromatography of a portion of this mixture on grade II neutral alumina using 95% toluene:5% ethyl acetate for elution afforded a sample of Compound IV which was converted to a hydrogen oxalate salt in acetone, mp 172°–174°.

Anal. calcd for $C_{20}H_{27}NO_4.C_2H_2O_4$: C, 60.68; H, 6.71; N, 3.22.

Found: C, 60.32; H, 6.83; N, 3.01.

(B)

11β-Hydroxy-6-hydroxymethyl-8-methoxy-3-methyl-11α-(2-methylallyl)-1,2,3,4,5,6-hexahydro-2,6-methano-3-benzazocine Fumarate (V)

A solution of Compound III (1.03 g; 0.003 mole) in THF (10 ml) was added to a mixture of $LiAlH_4$ (0.34 g) in THF (10 ml) and heated at reflux for 4 hours. This was cautiously treated with 1 ml of saturated $Na_2SO_4$ containing some NaOH and stirred, with warming, until the solids were white. The solids were removed by filtration and the filtrate was concentrated. The resultant oil was converted to a fumarate salt in 1-propanol, mp 186°–188°.

Anal. calcd for $(C_{19}H_{27}NO_3)_2.C_4H_4O_4$: C, 67.17; H, 7.79; N, 3.73.

Found: C, 67.03; H, 7.91; N, 3.67.

(C)

14β-Hydroxy-3-methoxy-7,7,17-trimethyl-6-oxamorphinan Hydrochloride (VI, BL-6016A)

A solution of Compound V base (17 g; 0.053 mole) in 180 ml of 10 N $H_2SO_4$ was heated on a steam bath for 6 hours, then stored at 20° for 16 hours. The reaction mixture was cautiously poured into a mixture of ice-concentrated $NH_4OH$ (150 ml) and extracted with $CH_2Cl_2$. Drying and concentration of the extract gave VI as an oil (16.3 g) which was converted to a hydrochloride salt in 2-propanol (87% yield), mp 184°–185°.

Anal. calcd for $C_{19}H_{27}NO_3.HCl$: C, 64.48; H, 7.97; N, 3.96.

Found: C, 64.15; H, 7.95; N, 4.06.

(D) 3-Methoxy-7,7,17-trimethyl-6-oxamorphin-8-ene Hydrochloride (VII, BL-6027A)

A mixture of 14β-hydroxy-3-methoxy-7,7,17-trimethyl-6-oxamorphinan (VI) (0.033 mol from 11.7 g hydrochloride), thionyl chloride (115 ml) and pyridine (2.6 g) was warmed at 40° for 24 hours. The thionyl chloride was removed at reduced pressure. The residue was treated with ice-water, made basic with $K_2CO_3$ and extracted with $CH_2Cl_2$. Drying ($MgSO_4$) and concentration of the extracts gave VII as an oil. A small portion of this oil was converted to a crystalline hydrochloride in 2-propanol, mp 243°–250° (decomp).

Anal. calcd for $C_{19}H_{25}NO_2.HCl$: C, 67.94; H, 7.80; N, 4.17.

Found: C, 67.43; H, 7.73; N, 4.26; $H_2O$, 0.48.

(E) 3-Methoxy-7,7,17-trimethyl-6-oxamorphinan Hydrochloride (VIII, BL-6028A)

A solution of VII (9.4 g, 0.031 mol) in ethanol (100 ml) was hydrogenated in a Parr Hydrogenator at 46 psi using 2 g $PtO_2$ as catalyst for 90 hours. The catalyst was removed by filtration and the filtrate concentrated. The resultant oil was converted to a crystalline hydrochloride salt in 2-propanol (7.6 g), mp 254°–260° (decomp).

Anal. calcd for $C_{19}H_{27}NO_2.HCl$: C, 67.54; H, 8.35; N, 4.15.

Found: C, 67.39; H, 8.47; N, 4.44.

EXAMPLE 2

3-Hydroxy-7,7,17-trimethyl-6-oxamorphinan (IX, BL-6092)

A mixture of VIII from Example 1, above, (0.6 g; 0.002 mol) and sodium thioethoxide (0.034 mol) (prepared from sodium hydride and ethyl mercaptan) in 40 ml DMF was heated at reflux for 4 hours. The solvent was removed at reduced pressure. The residue was treated with water, acidified with 6 N hydrochloric acid and washed with ether. The aqueous layer was filtered, basified with concentrated ammonium hydroxide and extracted with $CH_2Cl_2$. Drying ($MgSO_4$) and concentration gave an oil which was crystallized from acetonitrile to give IX as an acetonitrile solvate, mp 104°–105°.

Anal. calcd for $C_{18}H_{25}NO_2.C_2H_3N$: C, 73.13; H, 8.59; N, 8.53.

Found: C, 73.25; H, 8.61; N, 8.15.

EXAMPLE 3

3-Methoxy-7,7-dimethyl-6-oxamorphinan Hydrochloride (XI, BL-6084A)

A mixture of VIII base (from 6.5 g hydrochloride salt, 0.019 mol), $K_2CO_3$ (9 g), phenylchloroformate (9 g, 0.057 mol) and 75 ml toluene was heated at reflux with stirring for 20 hours. The cooled reaction mixture was treated with water (50 ml). The toluene layer was separated, washed with dil HCl, dried ($Na_2SO_4$) and concentrated to give crude X. This material was taken up in 2-propanol (300 ml), treated with water (75 ml) and KOH (36 g) and heated at reflux for 44 hours. The 2-propanol was removed at reduced pressure. The aqueous mixture was extracted with $CH_2Cl_2$ to give XI. This was converted to a hydrochloride salt in 2-propanol-ethyl acetate (5.7 g, 91%). The analytical sample was recrystallized from EtOAc-MeOH, mp 264°–268°.

Anal. calcd for $C_{18}H_{25}NO_2.HCl$: C, 66.75; H, 8.09; N, 4.33.

Found: C, 66.68; H, 7.91; N, 4.31.

EXAMPLE 4

17-Cyclopropylmethyl-7,7-dimethyl-3-methoxy-6-oxamorphinan Hydrochloride (XIII, BL-6085A)

A solution of XI base (2 g; 0.007 mol) in 25 ml $CH_2Cl_2$ and 5 ml triethylamine was cooled in ice-water bath and treated with 1.1 ml cyclopropane carboxylic acid chloride. This was stirred for ½ hour with cooling and 1½ hours while allowing to warm to 20°. Water was added and the mixture concentrated. The residue was treated with dilute HCl and extracted with toluene. The toluene extracts were washed with water, dilute $Na_2CO_3$, dried ($K_2CO_3$), filtered and concentrated to give XII. This material was reduced with $LiAlH_4$ (0.5 g) in THF (20 ml) at reflux for 16 hours to give Compound XIII which was isolated as a hydrochloride salt from 2-propanol, mp 259°–265° (decomp).

Anal. calcd for $C_{22}H_{31}NO_2.HCl$: C, 69.91; H, 8.54; N, 3.71.

Found: C, 69.57; H, 8.39; N, 3.79.

EXAMPLE 5

17-Cyclopropylmethyl-7,7-dimethyl-3-hydroxy-6-oxamorphinan Hydrochloride (XIV, BL-6097A)

Compound XIII, prepared in Example 4, was O-demethylated with sodium thioethoxide by the general procedure described in Example 2. The product was purified as a hydrochloride salt from ethanol, mp >250°.

Anal. calcd for $C_{21}H_{29}NO_2.HCl$: C, 69.30; H, 8.31; N, 3.85.

Found: C, 69.24; H, 8.10; N, 4.04.

EXAMPLE 6

17-Cyclobutylmethyl-7,7-dimethyl-3-methoxy-6-oxamorphinan Hydrochloride (XVI, BL-6127A)

Acylation of Compound XI, prepared in Example 3, with cyclobutane carboxylic acid chloride by the general procedure described in Example 4 gave Compound XV. Reduction of this material with excess sodium bis(2-methoxyethoxy)-aluminum hydride in tetrahydrofuran for 20 hours at 20° gave Compound XVI which was purified as a hydrochloride salt from ethanol-ethyl acetate, mp 236°–244° (decomp).

Anal. calcd for $C_{23}H_{33}NO_2.HCl$: C, 70.47; H, 8.74; N, 3.57.

Found: C, 70.72; H, 8.79; N, 3.47.

EXAMPLE 7

17-Cyclobutylmethyl-7,7-dimethyl-3-hydroxy-6-oxamorphinan Hydrochloride (XVII, BL-6142A)

Compound XVI, prepared in Example 6, was O-demethylated with sodium thioethoxide by the general procedure described in Example 2. The product was purified as a hydochloride salt from 95% ethanol, mp >250°.

Anal. calcd for $C_{22}H_{31}NO_2.HCl$: C, 69.91; H, 8.54; N, 3.71.

Found: C, 69.72; H, 8.60; N, 3.66.

EXAMPLE 8

3-Acetoxy-17-cyclopropylmethyl-7,7-dimethyl-6-oxamorphinan

Equimolar amounts of 17-cyclopropylmethyl-7,7-dimethyl-3-hydroxy-6-oxamorphinan (XIV, prepared in Example 5), acetyl chloride and pyridine are mixed together in dry methylene chloride and heated at reflux temperature for 3 hours to produce the title compound.

EXAMPLE 9

17-Cyclopropylmethyl-7,7-dimethyl-3-nicotinoyl-6-oxamorphinan

Equimolar amounts of 17-cyclopropylmethyl-7,7-dimethyl-3-hydroxy-6-oxamorphinan (XIV, prepared in Example 5), nicotinoyl chloride hydrochloride and pyridine are mixed together in dry methylene chloride and heated at reflux temperature for 3 hours to produce the title compound.

EXAMPLE 10

17-Allyl-7,7-dimethyl-3-methoxy-6-oxamorphinan

A mixture of 3-methoxy-7,7-dimethyl-6-oxamorphinan (XI, prepared in Example 3) (0.005 m), allyl bromide (0.006 m) and potassium carbonate (2 g) in 20 ml of acetonitrile is heated at reflux for 18 hours. The mixture is filtered and the filtrate concentrated. The residue is treated with water and extracted with ethyl acetate. The extracts are dried ($Na_2SO_4$) and concentrated to give the title compound.

EXAMPLE 11

17-Allyl-7,7-dimethyl-3-hydroxy-6-oxamorphinan

17-Allyl-7,7-dimethyl-3-methoxy-6-oxamorphinan (prepared in Example 10) is demethylated by the general procedure of Example 2 to produce the title compound.

EXAMPLE 12

7,7-Dimethyl-17-(3',3'-dimethylallyl)-3-methoxy-6-oxamorphinan

The general procedure of Example 10 is repeated except that the allyl bromide utilized therein is replaced by an equimolar amount of 3,3-dimethylallyl bromide, and the title product is thereby produced.

EXAMPLE 13

3-Hydroxy-7,7-dimethyl-17-(3',3'-dimethylallyl)-6-oxamorphinan 7,7-Dimethyl-17-(3',3'-dimethylallyl)-3-methoxy-6-oxamorphinan (produced in Example 12) is demethylated by the general procedure of Example 2 to produce the title compound.

EXAMPLE 14

Spiro[cyclohexane-1,7'-(3'-methoxy-17'-methyl-6'-oxamorphinan)] (XXX)

(A)

6-Carbomethoxy-11α-(1-cyclohexenylmethyl)-11β-hydroxy-8-methoxy-3-methyl-1,2,3,4,5,6-hexahydro-2,6-methano-3-benzazocine (XXVI) And
6-Carbomethoxy-11β-(1-cyclohexenylmethyl)-11α-hydroxy-8-methoxy-3-methyl-1,2,3,4,5,6-hexahydro-2,6-methano-3-benzazocine (XXVII)

An ice-cooled mixture of magnesium chips (30 g) in 50 ml of THF is treated with 5 ml of a solution of 1-chloromethylcyclohexene (14.4 g; 0.11 mole) [Bull. Chem. Soc. Japan, 44, 1885 (1971)] in 80 ml of THF. After the reaction starts, the remainder of the solution is added over a period of 30 minutes, and stirring is continued for 1 hour longer. This Grignard reagent is filtered through glass wool and added to a solution of Compound II (17.4 g; 0.06 mole) in 120 ml of THF maintained at −45° C. (dry ice-acetonitrile bath) over a period of 15 minutes. After 1 hour at −45° C., the reaction is treated with 250 ml of 10% NH$_4$Cl solution. The organic layer is separated, dried and concentrated to dryness to afford a mixture of Compounds XXVI and XXVII. This mixture is separated by chromatography on Grade II alumina.

(B)

11α-(1-Cyclohexenylmethyl)-11β-hydroxy-6-hydroxymethyl-8-methoxy-3-methyl-1,2,3,4,5,6-hexahydro-2,6-methano-3-benzazocine (XXVIII)

The general procedure of Example 1 Step (B) is repeated except that the Compound III utilized therein as starting material is replaced by an equimolar amount of Compound XXVI from Step (A), above, and the title compound is thereby produced.

(C)

Spiro[cyclohexane-1,7'-(14'β-hydroxy-3'-methoxy-17'-methyl-6'-oxamorphinan)] (XXIX)

The general procedure of Example 1 Step (C) is repeated except that the Compound V utilized therein as starting material is replaced by an equimolar amount of Compound XXVIII from Step (B), above, and the title compound is thereby produced.

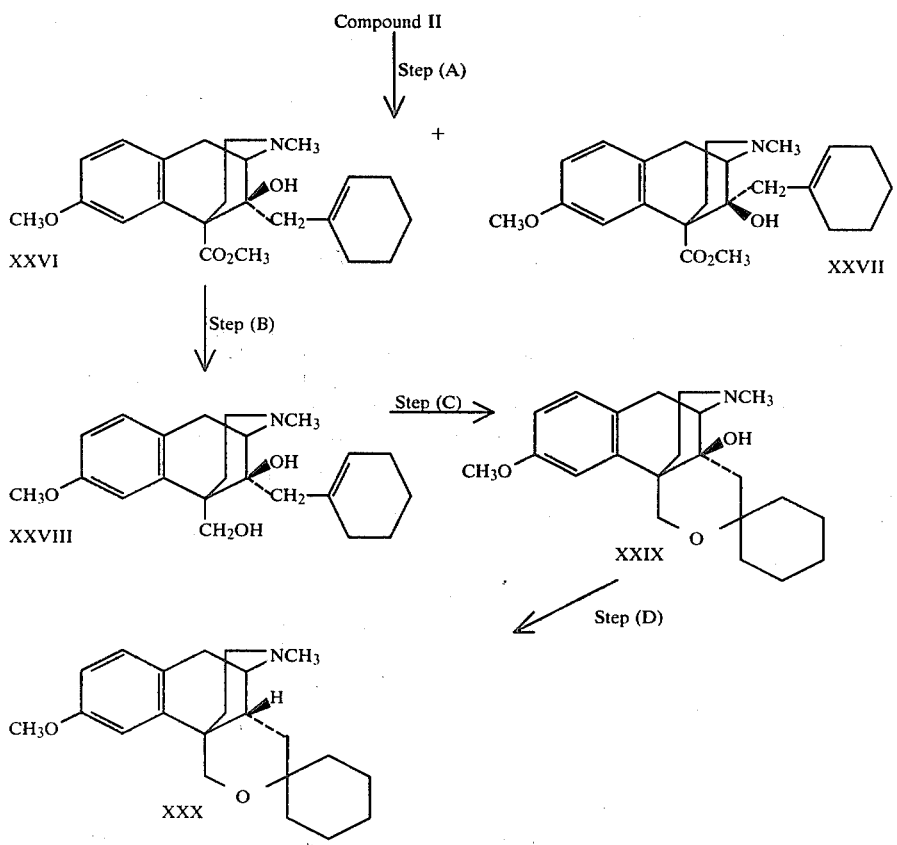

(D)

Spiro[cyclohexane-1,7'-(3'-methoxy-17'-methyl-6'-oxamorphinan)] (XXX)

The general procedure of Example 1 Steps (D) and (E) are repeated, except that the Compound VI utilized in Step (D) thereof is replaced by an equimolar amount of Compound XXIX from Step (C), above, and the title compound is thereby produced.

EXAMPLE 15

Compound XXX ⟶

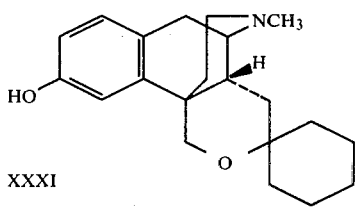

XXXI

Spiro[cyclohexane-1,7'-(3'-hydroxy-17'-methyl-6'-oxamorphinan)] (XXXI)

The general procedure of Example 2 is repeated except that the Compound VIII utilized therein as starting material is replaced by an equimolar amount of Compound XXX prepared in Example 14, above, and the title compound is thereby produced.

EXAMPLE 16

Spiro[cyclohexane-1,7'-(3'-methoxy-6'-oxamorphinan)] (XXXII)

Compound XXX ⟶

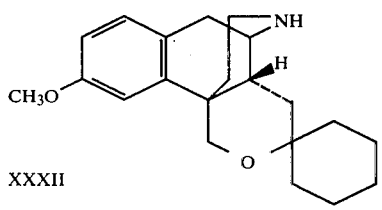

XXXII

The general procedure of Example 3 is repeated, except that the Compound VIII utilized therein is replaced by an equimolar amount of Compound XXX produced in Example 14, above, and the title compound is thereby produced.

EXAMPLE 17

Spiro[cyclohexane-1,7'-(17'-cyclopropylmethyl-3'-methoxy-6'-oxamorphinan)] (XXXIII)

Compound XXXII ⟶

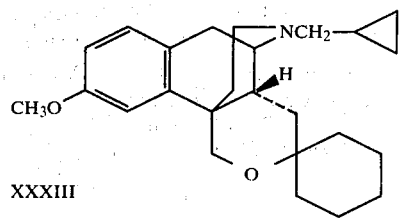

XXXIII

The general procedure of Example 4 is repeated, except that the Compound XI utilized therein as a starting material is replaced by an equimolar amount of Compound XXXII prepared in Example 16, above, and the title compound is thereby produced.

EXAMPLE 18

Spiro[cyclohexane-1,7'-(17'-cyclopropylmethyl-3'-hydroxy-6'-oxamorphinan)] (XXXIV)

Compound XXXIII ⟶

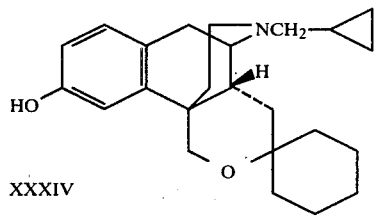

XXXIV

The general procedure of Example 5 is repeated, except that the Compound XII utilized therein as starting material is replaced by an equimolar amount of Compound XXXIII prepared in Example 18, above, and the title compound is thereby produced.

EXAMPLE 19

Spiro[tetrahydropyran-4,7'-(3'-methoxy-17'-methyl-6'-oxamorphinan)] (XXXV)

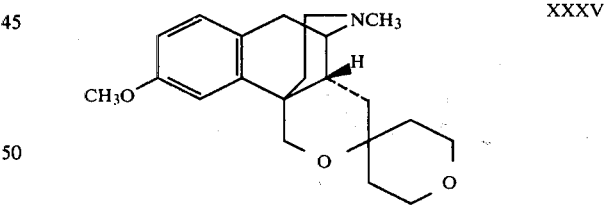

XXXV

The general procedure of Example 14, Steps (A)–(D), is repeated, except that the 1-chloromethylcyclohexene utilized therein is replaced by an equimolar amount of 4-chloromethyl-3,6-dihydropyran, and the title compound is thereby produced.

4-Chloromethyl-3,6-dihydropyran is prepared by dissolving 0.1 mole of 3,6-dihydro-4-pyranmethanol [prepared as described in Kagaku Kyokai Shi, 25 (4), 317 (1967); Chem. Abstr., 67, 11390 m (1967)] in 100 ml of methylene chloride and adding a solution of 0.2 mole of thionyl chloride in 25 ml of methylene chloride. The resulting solution is heated at reflux temperature for 1–2 hours, cooled and treated with ice-water. The organic layer is separated, washed with 5% aqueous $NaHCO_3$, dried ($Na_2SO_4$) and concentrated to give crude 4- chloromethyl-3,6-dihydropyran. This product is purified by distillation and is then utilized in the above procedure.

EXAMPLE 20

Spiro[tetrahydrothiopyran-4,7'-(3'-methoxy-17'-methyl-6'-oxamorphinan)] (XXXVI)

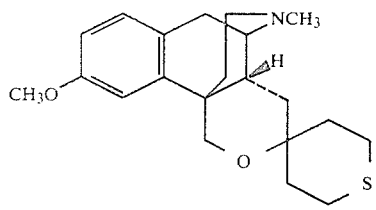
XXXVI

The general procedure of Example 14, Steps (A)-(D), is repeated, except that the 1-chloromethylcyclohexene utilized therein is replaced by an equimolar amount of 4-chloromethyl-3,6-dihydrothiopyran [prepared as described in Japan Kokai 73/91083 (*Chem. Abstr.*, 80, 133257 n (1974)], and the title compound is thereby produced.

We claim:

1. A compound of the formula

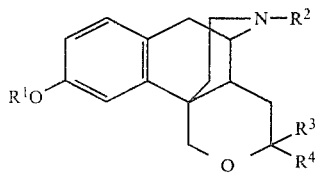
I wherein $R^1$ is hydrogen, (lower)alkyl, (lower)alkanoyl or nicotinoyl; $R^2$ is hydrogen, (lower)alkyl, propargyl allyl, 3,3-dimethylallyl, cyclopropylmethyl, cyclobutylmethyl,

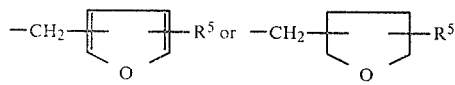

in which $R^5$ is hydrogen or (lower)alkyl, and $R^3$ and $R^4$ are the same or different and are (lower)alkyl, or $R^3$ and $R^4$, when taken together with the carbon atom to which they are attached, represent a spiroalkyl group of from 4 to 6 carbon atoms or a spiro moiety of the formula

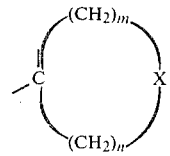

in which X is oxygen or sulfur, m is 2 or 3 and n is 1 or 2; or a pharmaceutically acceptable salt thereof.

2. A compound of claim 1 wherein $R^1$ is hydrogen or (lower)alkyl, $R^2$ is hydrogen, (lower)alkyl, cyclopropylmethyl or cyclobutylmethyl, and $R^3$ and $R^4$ are the same or different and are each (lower)alkyl; or a pharmaceutically acceptable salt thereof.

3. A compound of claim 1 wherein $R^1$ is hydrogen or methyl, $R^2$ is hydrogen, methyl, cyclopropylmethyl or cyclobutylmethyl, and $R^3$ and $R^4$ are each methyl; or a pharmaceutically acceptable salt thereof.

4. 3-Methoxy-7,7-dimethyl-6-oxamorphinan or a nontoxic, pharmaceutically acceptable salt thereof.

5. The (−)-isomer of the compound of claim 4 or a nontoxic, pharmaceutically acceptable salt thereof.

6. 17-Cyclopropylmethyl-7,7-dimethyl-3-methoxy-6-oxamorphinan or a nontoxic, pharmaceutically acceptable salt thereof.

7. The (−)-isomer of the compound of claim 6 or a nontoxic, pharmaceutically acceptable salt thereof.

8. 17-Cyclopropylmethyl-7,7-dimethyl-3-hydroxy-6-oxamorphinan or a nontoxic, pharmaceutically acceptable salt thereof.

9. The (−)-isomer of the compound of claim 8 or a nontoxic, pharmaceutically acceptable salt thereof.

10. 17-Cyclobutylmethyl-7,7-dimethyl-3-methoxy-6-oxamorphinan or a nontoxic, pharmaceutically acceptable salt thereof.

11. The (−)-isomer of the compound of claim 10 or a nontoxic, pharmaceutically acceptable salt thereof.

12. 17-Cyclobutylmethyl-7,7-dimethyl-3-hydroxy-6-oxamorphinan or a nontoxic, pharmaceutically acceptable salt thereof.

13. The (−)-isomer of the compound of claim 12 or a nontoxic, pharmaceutically acceptable salt thereof.

* * * * *